(12) United States Patent
Jackson et al.

(10) Patent No.: US 9,790,150 B2
(45) Date of Patent: Oct. 17, 2017

(54) PROCESSES FOR PRODUCING BRANCHED FLUOROALKYL OLEFINS

(71) Applicant: THE CHEMOURS COMPANY FC, LLC, Wilmington, DE (US)

(72) Inventors: Andrew Jackson, Newark, DE (US); Sheng Peng, Hockessin, DE (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/813,415

(22) Filed: Jul. 30, 2015

(65) Prior Publication Data
US 2016/0046547 A1 Feb. 18, 2016

Related U.S. Application Data

(60) Provisional application No. 62/036,237, filed on Aug. 12, 2014.

(51) Int. Cl.
| | |
|---|---|
| *C07C 17/383* | (2006.01) |
| *C07C 17/278* | (2006.01) |
| *C07C 19/14* | (2006.01) |
| *C07C 17/25* | (2006.01) |
| *C07C 19/12* | (2006.01) |

(52) U.S. Cl.
CPC ............ *C07C 17/278* (2013.01); *C07C 17/25* (2013.01); *C07C 17/383* (2013.01); *C07C 19/12* (2013.01); *C07C 19/14* (2013.01)

(58) Field of Classification Search
CPC ..... C07C 17/278; C07C 19/14; C07C 17/383; C07C 19/12; C07C 17/25; C07C 19/10; C07C 21/18
USPC ................................ 570/137, 155, 156, 172
See application file for complete search history.

(56) References Cited

U.S. PATENT DOCUMENTS

| | | | |
|---|---|---|---|
| 2,700,688 A | 1/1955 | Crane | |
| 4,228,107 A | 10/1980 | Holland et al. | |
| 2003/0060670 A1 | 3/2003 | Nair et al. | |
| 2005/0245773 A1 | 11/2005 | Mukhopadhyay et al. | |
| 2012/0175137 A1* | 7/2012 | Hedrick | A62D 1/00 169/5 |
| 2014/0058141 A1* | 2/2014 | Nappa | C07C 17/278 570/172 |

FOREIGN PATENT DOCUMENTS

| | | |
|---|---|---|
| FR | 1361255 A | 5/1964 |
| FR | 2627180 A1 | 8/1989 |
| WO | 9705090 A1 | 2/1997 |
| WO | 2012067865 A1 | 5/2012 |

OTHER PUBLICATIONS

Haszeldine, Addition of Free Radicals to Unsaturated Systems, Journal of the Chemical Socitey, 1953.
Fleming et al., Addition of Free Radicals to Unsaturated Systems, Journal of Chemical Society, 1973.
Tarrant et al., The Peroxide Initiated Addition of Some Polyflurorcholoro and Poly Flurobromoalkanes to some Hydrocarbon Ofefins, Journal of Organic Chemistry, vol. 34, 4, 1969.

* cited by examiner

*Primary Examiner* — Jafar Parsa (57) ABSTRACT

Processes for producing branched fluoroalkyl olefins are disclosed. In addition, novel halo-fluoroalkane intermediates are disclosed that may be used in the branched fluoroalkyl olefin production processes. Non-limiting examples of branched fluoroalkyl olefins include branched fluorobutenes, such as 1,3,4,4,4-pentafluoro-3-trifluoromethyl)but-1-ene (HFO-1438ezy). In some aspects, there is disclosed a method for dehydrobrominating 4-bromo-1,1,1,2,4-pentafluoro-2-(trifluoromethyl)butane to produce 1,3,4,4,4-pentafluoro-3-(trifluoromethyl)but-1-ene (HFO-1438ezy).

8 Claims, 5 Drawing Sheets

PROCESSES FOR PRODUCING BRANCHED FLUOROALKYL OLEFINS

CROSS-REFERENCE TO RELATED APPLICATIONS

This application claims priority to U.S. Provisional No. 62/036,237, filed on Aug. 12, 2014, which is hereby incorporated in its entirety.

TECHNICAL FIELD

The disclosure herein relates to fluoroalkyl olefins. Particularly, the disclosure herein relates to processes for the production of branched fluoroalkyl olefins. In addition, the disclosure relates to novel halo-fluoroalkane intermediates and processes for making the same.

BRIEF SUMMARY

This Summary is provided to introduce a selection of concepts in a simplified form that are further described below in the Detailed Description. This Summary is not intended to identify key features or essential elements of the claimed subject matter, nor is it intended to be used as an aid in determining the scope of the claimed subject matter.

Current processes for producing branched fluoroalkyl olefins may include the use of secondary fluoroalkyl iodides. However, the use of iodides can be expensive. Therefore, there is a need for lower cost processes for the production of branched fluoroalkyl olefins.

Accordingly, aspects herein describe processes for producing branched fluoroalkyl olefins. In addition, aspects herein describe novel halo-fluoroalkane intermediates that may be used in the branched fluoroalkyl olefin production processes, as well as processes for making the novel halo-fluoroalkane intermediates.

In Embodiment 1, the invention is directed to a production process comprising the step of contacting a halo-fluoroalkane reactant with an olefinic reactant in a reaction vessel to produce a halo-fluoroalkane intermediate, wherein each of said halo-fluoroalkane reactant and said halo-fluoroalkane intermediate is substituted by bromine or chlorine.

In Embodiment 2, the invention is directed to the process according to Embodiment 1, further comprising the step of converting said halo-fluoroalkane intermediate into one or more branched fluoroalkyl olefins.

In Embodiment 3, the invention is directed to the process according to Embodiment 2, wherein said converting comprises dehydrohalogenating said halo-fluoroalkane intermediate by contacting said halo-fluoroalkane intermediate with an aqueous base and heating said reaction vessel to a temperature of between about 35 and about 100° C.

In Embodiment 4, the invention is directed to the process according to Embodiment 3, wherein said contacting is done in the presence of a phase transfer catalyst.

In Embodiment 5, the invention is directed to the process according to Embodiment 1, wherein said contacting is done in the presence of: a) a metal or a metal salt; and, b) a ligand.

In Embodiment 6, the invention is directed to the process according to Embodiment 5, wherein the metal or metal salt is selected from the group consisting of iron, copper and the chloride and bromide salts thereof, and wherein the ligand is selected from the group consisting of tributyl phosphate, triphenyl phosphine.

In Embodiment 7, the invention is directed to the process according to Embodiment 2, wherein said halo-fluoroalkyl intermediate comprises 4-bromo-1,1,1,2,4-pentafluoro-2-(trifluoromethyl)butane and said one or more branched fluoroalkyl olefins comprises 1,3,4,4,4-pentafluoro-3-(trifluoromethyl)but-1-ene (HFO-1438ezy).

In Embodiment 8, the invention is directed to the process according to Embodiment 7, wherein said converting comprises the step of heating said 4-bromo-1,1,1,2,4-pentafluoro-2-(trifluoromethyl)butane in said reaction vessel to a temperature of between about 185 and about 220° C.

In Embodiment 9, the invention is directed to the process according to Embodiment 8, wherein said heating step is conducted in the presence of a catalyst.

In Embodiment 10, the invention is directed to the process according to Embodiment 7, wherein said reactor is heated to said temperature while purging with an inert gas, and said 4-bromo-1,1,12,3-pentafluoro-2-(trifluoromethyl)butane is fed to said reactor at a feed rate that results in a contact time of between about 30 and about 60 seconds.

In Embodiment 11, the invention is directed to a halo-fluoroalkane compound having a formula selected from the group consisting of:

wherein R is selected from the group consisting of —CH$_2$CHFBr, —CH$_2$CCl$_2$Br, —CH$_2$CHClBr and —CH$_2$CF$_2$Br;

wherein R is selected from the group consisting of —CH$_2$CH$_2$Cl, —CH$_2$CCl$_3$, —CH$_2$CF$_2$Cl, —CH$_2$CHCl$_2$ and —CH$_2$CHClF; and, wherein R is selected from the group consisting of —CH$_2$CCl$_2$Br, —CH$_2$CF$_2$Br, —CH$_2$CHClBr and —CH$_2$CHFBr, and purified forms thereof.

In Embodiment 12, the invention is directed to the halo-fluoroalkane compound of Embodiment 11 having the formula:

wherein R is —CH$_2$CHFBr, and purified forms thereof.

In Embodiment 13, the invention is directed to a method for producing 1,3,4,4,4-pentafluoro-3-(trifluoromethyl)but-1-ene (HFO-1438ezy), the method comprising the step of dehydrobrominating 4-bromo-1,1,1,2,4-pentafluoro-2-(trifluoromethyl)butane.

In Embodiment 14, the invention is directed to the method according to Embodiment 13, wherein said dehydrobrominating step proceeds in the liquid phase and comprises contacting said 4-bromo-1,1,1,2,4-pentafluoro-2-(trifluoromethyl)butane with a base aqueous or alcoholic solution in the presence of a phase transfer catalyst at a temperature of between about 0 and about 200° C.

In Embodiment 15, the invention is directed to the method according to Embodiment 13, wherein said dehydrobrominating step proceeds in the vapor phase in the presence of a catalyst selected from the group consisting of carbon, alumina oxides and chrome oxides.

In Embodiment 16, the invention is directed to the method according to Embodiment 15, wherein said dehydrobrominating proceeds in a reactor with inert gas purge at a temperature of between about 185 and about 220° C.

In Embodiment 17, the invention is directed to the method according to Embodiment 16, wherein said 4-bromo-1,1,12,3-pentafluoro-2-(trifluoromethyl)butane is fed to said reactor at a feed rate that results in a contact time of between about 30 and about 60 seconds.

In Embodiment 18, the invention is directed to the method according to Embodiment 13 further comprising the step of purifying said 1,3,4,4,4-pentafluoro-3-trifluoromethyl)but-1-ene (HFO-1438ezy) by a separation method selected from the group consisting of absorption, extraction, chromatography and recrystallization.

In Embodiment 19, the invention is directed to the method according to Embodiment 13 further comprising the step of purifying said 1,3,4,4,4-pentafluoro-3-trifluoromethyl)but-1-ene (HFO-1438ezy) by distillation.

In Embodiment 20, the invention is directed to the purified form of 1,3,4,4,4-pentafluoro-3-trifluoromethyl)but-1-ene (HFO-1438ezy) that is the product of the process according to Embodiment 19.

BRIEF DESCRIPTION OF THE DRAWINGS

Aspects herein are described in detail with reference to the attached figures.

DETAILED DESCRIPTION

For purposes of clarity, certain terms used herein are defined. Thus, as used herein the terms "alkane" and "alkyl" shall be understood to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. In an embodiment, if the number of carbon atoms is not specified, "alkyl" refers to $C_1$-$C_{12}$ alkyl and in a further embodiment, "alkyl" refers to $C_1$-$C_6$ alkyl.

As used herein the term "fluoroalkane" shall be understood to mean a $C_3$-$C_6$ alkane that is substituted in at least one location with a fluorine. Any carbon may be substituted. The generic formula is $CR_3$—$CRX$—$CR_3$, wherein each R is independently selected from the group consisting of Cl, Br, F, H, alkyl and $CF_3$, and X is selected from the group consisting of F, Cl and Br.

As used herein the term "dihalo-fluoroalkane" shall be understood to mean a $C_3$-$C_6$ fluoroalkane that is further substituted in at least one location with two halogens. The generic formula is $CF_3$—$CRX$—$CR_2X$, wherein each R is independently selected from the group consisting of Cl, Br, F, H, alkyl and $CF_3$, and X is selected from the group consisting of F, Cl and Br.

As used herein the term "olefin" shall be understood to mean a $C_2$-$C_6$ alkene.

As used herein the term "fluoroolefin" shall be understood to mean a $C_3$-$C_6$ olefin that incorporates at least one $CF_3$ group. The generic formula is $CF_3$—$CR$=$CR_2$, wherein each R is independently selected from the group consisting of Cl, Br, F, H, alkyl and $CF_3$.

As used herein the term "halo-fluoroalkane intermediate" shall be understood to mean the branched product of the reaction between a halo-fluoroalkane reactant and an olefinic reactant.

As used herein the term "branched fluoroalkyl olefin" shall be understood to mean the $C_2$-$C_6$ product of the dehydrohalogenation of a halo-fluoroalkane intermediate. Non-limiting examples of branched fluoroalkyl olefins include branched fluorobutenes, such as 1,3,4,4,4-pentafluoro-3-trifluoromethyl) but-1-ene (HFO-1438ezy), E-$(CF_3)_2$CF—CH=CFH, E-$(CF_3)_2$CF—CH=CClH, $(CF_3)_2$ CF—CH=$CF_2$, $(CF_3)_2$CF—CH=$CCl_2$, $(CF_3)_2$CF—CH=$CH_2$, $(CF_3)_2$CCl—CH=$CH_2$, E-$(CF_3)_2$CCl—CH=$CCl_2$, $(CF_2Br)(CF_3)$CF—CH=$CH_2$, E-$(CF_2Br)(CF_3)$ CF—CH=CHCl, E-$(CF_2Br)(CF_3)$CF—CH=$CF_2$, E-$(CF_2Br)(CF_3)$CF—CH=$CCl_2$ and E-$(CF_2Br)(CF_3)$CF—CH=CHF.

As used herein the term "ligand" shall be understood to mean an agent that complexes a metal or a metal salt, making it more soluble in the reaction medium. Non-limiting examples of ligands include phosphorous containing ligands such as trialkyl phosphates and triphenyl phosphines, and nitrogen containing ligands such as 2,2-Bipyridyl.

As used herein the term "metal salt" shall be understood to include transition metal salts. $FeX_3$, $FeX_2$, CuX and $CuX_2$, wherein X is F, Cl or Br, are non-limiting examples of metal salts.

As used herein the term "aqueous and/or alcoholic base" shall be understood to mean an alkali metal base. Non-limiting examples include KOH and NaOH.

As used herein the term "phase transfer catalyst" shall be understood to mean a catalyst that facilitates the migration of a reactant from one phase into another phase where reaction occurs. Non-limiting examples of phase transfer catalysts include quaternary ammonium and phosphonium salts.

As used herein the term "inert gas" shall be understood to include noble gases. $N_2$, He and Ar are non-limiting examples of inert gases.

Any carbon with otherwise unsatisfied valences in the text, schemes, examples and tables herein is assumed to have the sufficient number of hydrogen atom(s) to satisfy the valences.

Although U.S. Provisional No. 62/036,237 is incorporated by reference in its entirety, there may be instances where terms of that document or any other incorporated document or passage may conflict with those of the present application. In such instances, the terms of the present application shall prevail.

Aspects herein describe processes for producing branched fluoroalkyl olefins. In addition, aspects herein describe novel halo-fluoroalkane intermediates that may be used in the processes for producing branched fluoroalkyl olefins. Further, processes for producing the novel halo-fluoroalkane intermediates are described.

Figure 1:
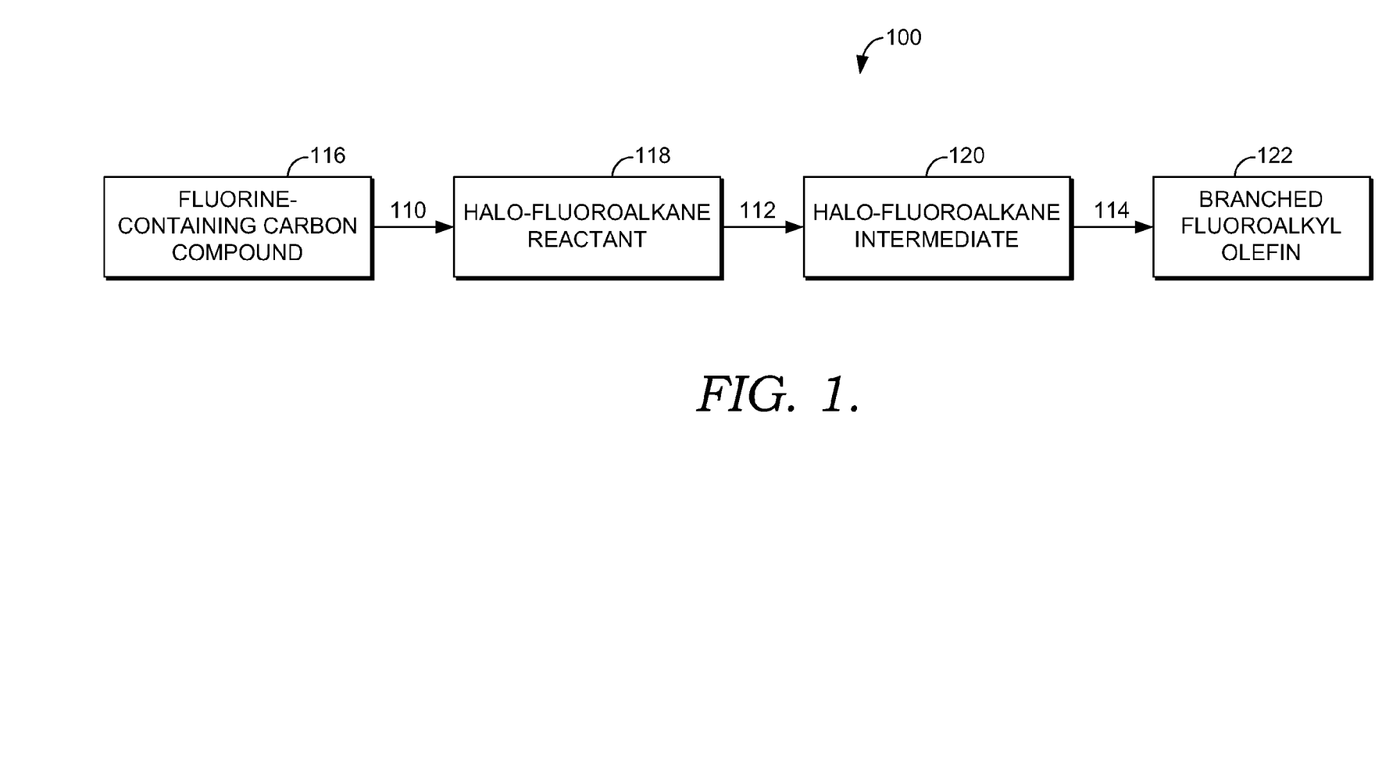
FIG. 1 depicts a multi-step process for the production of branched fluoroalkyl olefins.

FIG. 1 depicts an exemplary multi-step process 100 for the production of branched fluoroalkyl olefins. In various aspects, the exemplary multistep process 100 may include a step 110 that includes a process for the production of a halo-fluoroalkane reactant 118 from a fluorine-containing carbon compound 116. Further, in one or more aspects, the multi-step process 100 may include a step 112 that includes a process for the production of a halo-fluoroalkane intermediate 120 from the halo-fluoroalkane reactant 118. In addition, in various aspects, the multi-step process 100 may include the step 114 that includes a process for the production of a branched fluoroalkyl olefin 122 from the halo-fluoroalkane intermediate 120.

Figure 2:
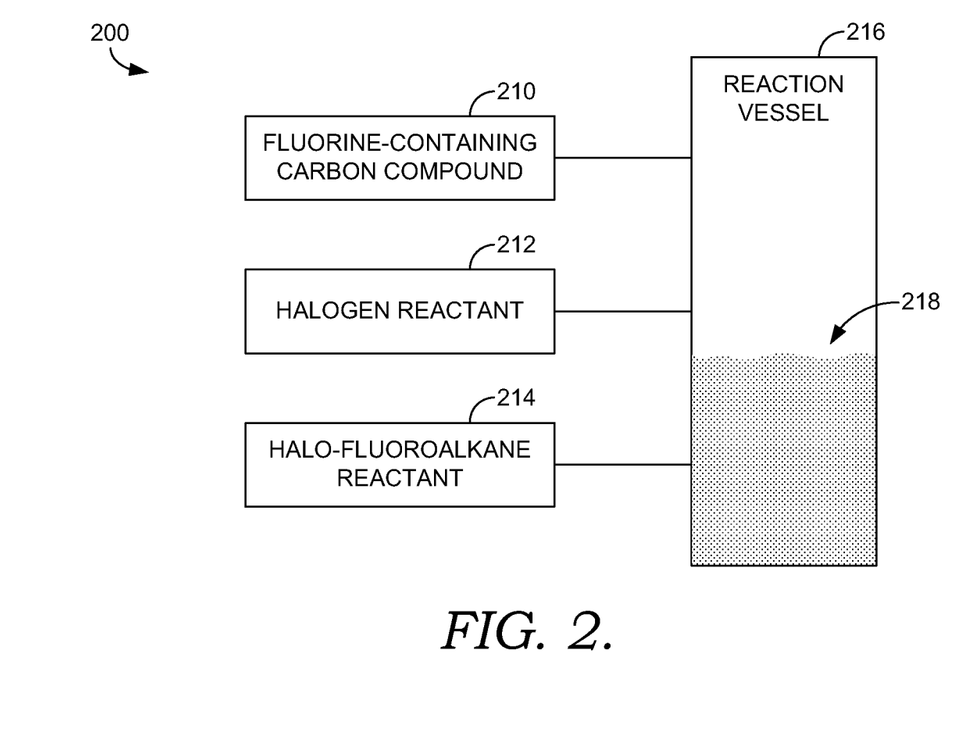
FIG. 2 depicts a schematic diagram of a system for the production of a halo-fluoroalkane reactant.

FIG. 2 depicts a system 200 that may be used for the production of halo-fluoroalkane reactants, such as the process described above with reference to step 110 of FIG. 1. The system 200 may include a fluorine-containing carbon compound reservoir 210 and/or a halogen reactant reservoir 212 coupled to a reaction vessel 216. The system 200 may be configured with these reaction reservoirs to produce a halo-fluoroalkane reactant within the halo-fluoroalkane reactant reservoir 214 and/or within at least a portion of the reaction vessel 216.

In various aspects, the reaction vessel 216 may be configured as a commercially operable reaction vessel. Such reaction vessels may include those reaction vessels configured to react compounds in the liquid phase and/or in the gas phase at predetermined pressures and/or temperatures. In one or more aspects, the reaction vessel 216 may include conduits for receiving reactants from the reservoirs 210 and 212. In the same or alternative aspects, conduits for providing product to the reservoir 214 may be included.

In one or more aspects, the halogen reactant can include bromine and/or chlorine, e.g., $Br_2$ and/or $Cl_2$. In certain aspects, the halogen reactant may not include iodine. In various aspects, the fluorine-containing carbon compound may include a fluoroolefin and/or a fluoroalkane. In or more aspects, the fluorine-containing carbon compound may include hexafluoropropylene (HFP).

In various aspects, one or more halogen reactants may be combined in a vessel, e.g., the reaction vessel 216, with one or more fluorine-containing carbon compounds to form a mixture 218. In such aspects, within the mixture 218, at least a portion of the fluorine-containing carbon compound, e.g., HFP, may be halogenated.

In various aspects, the halogenation of a fluoroolefin may include a thermal process. For example, the halogenation of a fluoroolefin may include exposing a fluoroolefin to a halogen, such as bromine or chlorine, in a reaction vessel at a predetermined temperature. In such aspects, the molar ratio of the fluoroolefin to the halogen may be about 1:1, 1.5:1, 2:1, 5:1, 1:5, 1:2, or 1:1.5. In one aspect, the predetermined temperature may be below the boiling point of the halogen. For example, a fluoroolefin and bromine may be combined into a reaction vessel at a temperature of about 100° C.

An exemplary process for producing a halo-fluoroalkane reactant may include configuring the vessel 216 as a preheated shaker tube (e.g., a 400 mL Hastelloy® shaker tube) and adding a fluoroolefin thereto, at a rate of 1 mL per minute. Further, this exemplary process may include maintaining this reaction mixture at the preheated temperature (e.g., at 100° C.) for about 9 hours, then chilling the product mixture and washing it with an aqueous solution of sodium sulfite. This product mixture, may then be dried, e.g., in a molecular sieve. In certain aspects, this product mixture may include a dihalo-fluoroalkane, e.g., a dibromo-hexafluoro-propane. In one or more aspects, this dihalo-fluoroalkane may then be fluorinated to produce a halo-fluoroalkane reactant. In such aspects, the dihalo-fluoroalkane may be fluorinated by combining at least a portion of the dihalo-fluoroalkane with KF in conditions sufficient to produce the halo-fluoroalkane reactant.

Another exemplary process for thermally producing a halo-fluoroalkane reactant may include the gas phase bromination of a fluoroalkane, e.g., 2H-heptafluoropropane. This exemplary process may include configuring the reaction vessel 216 as a 12 inch by 5 inch Hastelloy® tube reactor and adding thereto a solid carbon matrix, e.g., coconut shell carbon. The vessel and the carbon matrix may then be heated to a desired temperature. In various aspects, the desired temperature may be at least about 350° C., 375° C., 400° C., 425° C., or 450° C., and/or not more than about 550° C., 525° C., or 500° C. In such aspects, the feed rates for the addition of the fluoroalkane and bromine may be adjusted to achieve the desired contact time with the carbon matrix. In one or more aspects, the desired contact time with the carbon matrix may be at least about 1 second, 10 seconds, 15 seconds, 20 seconds, 30 seconds, or 45 seconds, and/or not more than about 10 minutes, 5 minutes, 3 minutes or 1 minute. In various aspects, the ratio of the halogen to the fluorine-containing carbon compound may be at least about 1:5, 1:2, or 1:1.5, and/or not more than about 1:1, 1.1:1, 1.2:1, 1.3:1, 1.4:1, 2:1, or 5:1

In certain aspects, the halogenation of a fluoroolefin may include exposing a fluoroolefin to a halogen, such as bromine or chlorine, in a reaction vessel that is being irradiated by UV light. In such aspects, an exemplary process for producing a halo-fluoroalkane reactant may include configuring the reaction vessel 216 as a round bottom 500 mL flask equipped with a dry ice condenser. The flask may include a halogen in the liquid phase, e.g., liquid bromine. A gaseous fluoroolefin may be introduced, subsurface, to the liquid halogen in the flask. The fluoroolefin may be added until the solution becomes clear or until a desired amount of fluoroolefin is added. The material may then be washed, e.g., with 10% sodium sulfite, and the organic phase may be dried, e.g., with calcium sulfate. In one or more aspects, at least a portion of this organic phase may then be fluorinated to produce a halo-fluoroalkane reactant. In such aspects, at least a portion of this organic phase may be fluorinated with KF in conditions sufficient to produce the halo-fluoroalkane reactant.

Figure 3:
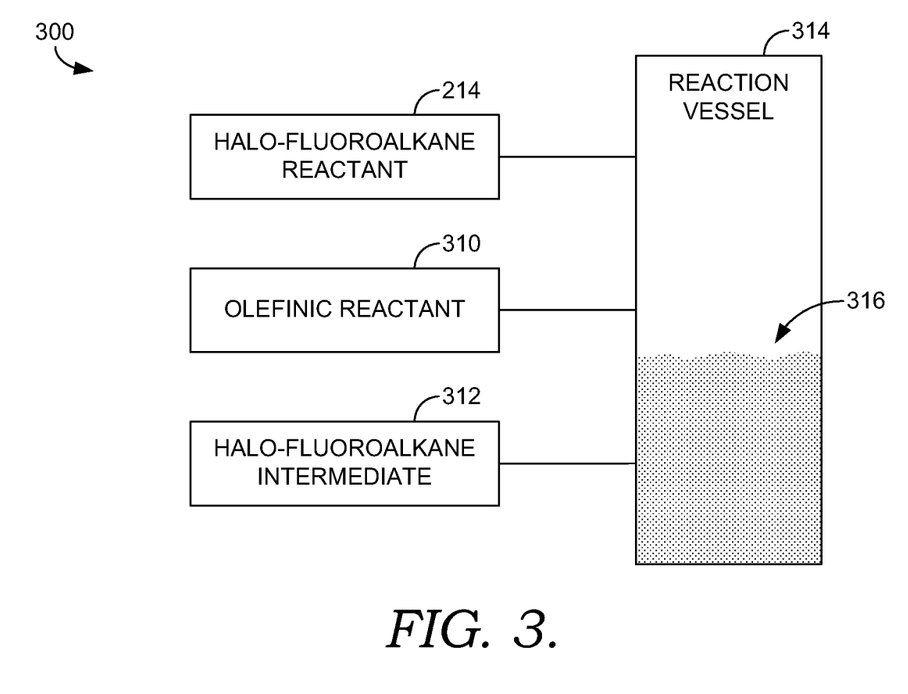
FIG. 3 depicts a schematic diagram of a system for the production of a halo-fluoroalkane intermediate.

Turning now to FIG. 3, a system 300 is depicted that includes a halo-fluoroalkane reactant reservoir 214 and an olefinic reactant reservoir 310 that may be coupled to a reaction vessel 314. The system 300 may be configured with these reaction reservoirs 214 and 310 to produce a halo-fluoroalkane intermediate within the halo-fluoroalkane intermediate reservoir 312 and/or within at least a portion of the reaction vessel 314.

In various aspects, the reaction vessel 314 may be configured as a commercially operable reaction vessel. Such reaction vessels may include those reaction vessels configured to react compounds in the liquid phase and/or in the gas phase at predetermined pressures and/or temperatures. In one or more aspects, the reaction vessel 314 may include conduits for receiving reactants from the reservoirs 214 and 310. In the same or alternative aspects, conduits for providing product to the reservoir 312 may be included.

The halo-fluoroalkane reactant may include any fluoroalkane substituted by one or more of bromine and/or chlorine. For example, in certain aspects, the halo-fluoroalkane reactant may comprise, consist essentially of, and/or consist of $CF_3CFBrCF_3$, $CF_3CCl_2CF_3$, and/or $CF_3CFBrCF_2Br$. In one or more aspects, the halo-fluoroalkane reactant may be selected from the group consisting of $CF_3CFBrCF_3$, $CF_3CCl_2CF_3$, and $CF_3CFBrCF_2Br$. In various aspects, the halo-fluoroalkane reactant may comprise, consist essentially of, and/or consist of a 1,2-dihalo fluoropropane, a 2,2-dihalo fluoropropane, and/or a 2-halo fluoropropane. In certain aspects, the halo-fluoroalkane reactant may not include iodine. In certain aspects, the halo-fluoroalkane reactant is a C3-C6 alkane substituted by at least one F, and further substituted by at least one of Cl and Br.

In various aspects, the olefinic reactant may include a $C_2$-$C_6$ alkene and/or a halo-alkene. In one or more aspects, the olefinic reactant may comprise, consist essentially of, and/or consist of $CH_2$=$CH_2$, $CH_2$=$CHF$, $CH_2$=$CHCl$, $CH_2$=$CF_2$, and/or $CH_2$=$CCl_2$.

In various aspects, one or more olefinic reactants may be combined in a vessel, e.g., the reaction vessel 314, with one or more halo-fluoroalkane reactants to form a mixture 316. In one or more aspects, in the mixture 316, the addition of one or more olefinic reactants to one or more halo-fluoroalkane reactants may occur.

In certain aspects, the addition of an olefinic reactant to a halo-fluoroalkane reactant may be carried out in the presence of additional materials. In such aspects, these additional materials may include one or more free radical initiators, such as peroxides, and/or azo compounds (e.g., Vazo® products from DuPont); one or more metals (e.g., Fe and/or Cu); and/or one or more metal salts (e.g., $FeX_3$, where X is a halide, and/or CuCl). Further, in various aspects, the addition of an olefinic reactant to a halo-fluoroalkane reactant may be carried out in the presence of one or more ligands, such as tributyl phosphate, triphenyl phosphine and/or 2,2-Bipyridyl. In one aspect, the addition of an olefinic reactant to a halo-fluoroalkane reactant may be carried out in the presence of Fe, and tributyl phosphate and/or triphenyl phosphine. In another aspect, the addition of an olefinic reactant to a halo-fluoroalkane reactant may be carried out in the presence of Fe, a metal salt, such as $FeCl_3$, and tributyl phosphate and/or triphenyl phosphine.

In one or more aspects, at least about 0.01 moles, 0.02 moles, 0.05 moles, 0.07 moles, or 0.1 moles, and/or not more than about 1 mole, 0.5 moles, 0.4 moles, 0.3 moles, or 0.2 moles of a metal (e.g., Fe) may be added for each mole of the halo-fluoroalkane reactant added (and/or for each mole of the olefinic reactant added). In certain aspects, at least about 0.0001 moles, 0.001 moles, 0.01 moles, or 0.1 moles, and/or not more than 0.5 moles, 0.25 moles, or 0.1 moles of a metal salt, e.g., iron III bromide, may be added for each mole of the halo-fluoroalkane reactant added. In various aspects, at least about 0.0001 moles, 0.001 moles, or 0.01 moles, and/or not more than about 0.5 moles, 0.25 moles, or 0.1 moles of ligand, e.g., tributyl phosphate, may be added for each mole of the halo-fluoroalkane reactant added.

In various aspects, the addition reaction may include exposing one or more olefinic reactants to one or more halo-fluoroalkane reactants in a reaction vessel, e.g., the vessel 314, at a predetermined temperature. In one or more aspects, the molar ratio of the olefinic reactant to the halo-fluoroalkane reactant, e.g., 2-bromoheptafluoropropane, present in the vessel may be about 1:1, 1.5:1, 2:1, 3.5:1, 5:1, 6:1, 7:1, 8:1, 1:8, 1:7, 1:6 1:5, 1:3.5, 1:2, or 1:1.5. In alternative aspects, the molar ratio of the olefinic reactant to the halo-fluoroalkane reactant may be about 0.01:1, 0.05:1, 0.1:1, 0.5:1, or 0.75:1. In certain aspects, the predetermined temperature may be at least about 75° C., 85° C., 90° C., 100° C., 125° C., or 150° C., and/or not more than about 300° C., 250° C., 200° C., or 175° C. In various aspects, the mixture, e.g., the mixture 316, of the olefinic reactant and the halo-fluoroalkane reactant may be held at the predetermined temperature for at least about 4 hours, 8 hours, 12 hours, 18 hours, or 24 hours, and/or not more than about 48 hours, 36 hours, or 30 hours.

An exemplary process for the addition of an olefinic reactant to a halo-fluoroalkane reactant may include configuring the reaction vessel 314 as a 400 ml shaker tube or a pressure reactor, where a metal, metal salt, and/or a ligand may be added thereto. Further, this exemplary process may include chilling the reaction vessel in a dry ice/acetone bath and adding the halo-fluoroalkane to the reaction vessel. The reaction vessel may then be flushed with liquid nitrogen prior to heating the reaction vessel at a predetermined temperature, such as the predetermined temperatures discussed above. The reaction vessel may be held at this predetermined temperature for at least about 1 hour, 1.5 hours, or 2 hours, and/or not more than about 5 hours, 4 hours, or 3 hours. Further, this exemplary process may include adding to the shaker tube an olefinic reactant at a rate of at least about 0.1 moles per hour, 0.25 moles per hour, or 0.5 moles per hour, and/or not more than about 2 moles per hour, 1.5 moles per hour, or 1 mole per hour. In addition, this exemplary process may include incubating this reaction mixture at the predetermined temperature for at least about 4 hours, 8 hours, 12 hours, 18 hours, or 24 hours, and/or not more than about 48 hours, 36 hours, or 30 hours. After the incubation period, the reaction vessel may be chilled in ice. The crude product, which may include a halo-fluoroalkane intermediate, may be collected by standard processes known to one skilled in the art. In one aspect, the resulting halo-fluoroalkane may be fluorinated with HF or metal fluorides to produce a halo-fluoroalkane intermediate.

In one or more aspects, the halo-fluoroalkane intermediate may comprise a branched carbon chain. In certain aspects, the halo-fluoroalkane intermediate may comprise bromine and/or chlorine. In various aspects, the halo-fluoroalkane intermediate may not comprise iodine. In one aspect, the halo-fluoroalkane intermediate may have the formula wherein R is selected from the group consisting of —$CH_2CHFBr$, —$CH_2CCl_2Br$, —$CH_2CHClBr$ and —$CH_2CF_2Br$. In various aspects, the halo-fluoroalkane intermediate may have the formula wherein R is selected from the group consisting of —CH₂CH₂Cl, —CH₂CCl₃, —CH₂CF₂Cl, —CH₂CHCl₂, and —CH₂CHClF. In certain aspects, the halo-fluoroalkane intermediate may have the formula wherein R is selected from the group consisting of —CH₂CCl₂Br, —CH₂CF₂Br, —CH₂CHClBr and —CH₂CHFBr. In certain aspects, the halo-fluoroalkane intermediate may have a formula selected from the group consisting of:

wherein R is selected from the group consisting of —CH₂CHFBr, —CH₂CCl₂Br, —CH₂CHCLBR and —CH₂CF₂Br;

wherein R is selected from the group consisting of —CH₂CH₂Cl, —CH₂CCl₃, —CH₂CF₂Cl, —CH₂CHCl₂ and —CH₂CHClF; and, wherein R is selected from the group consisting of —CH₂CCl₂Br, —CH₂CF₂Br, —CH₂CHClBr and —CH₂CHFBr. In one aspect, the halo-fluoroalkane intermediate may have the formula wherein R is —CH₂CHFBr, which may also be known as 4-bromo-1,1,1,2,4,-pentafluoro-2-(trifluoromethyl)butane.

Figure 4:
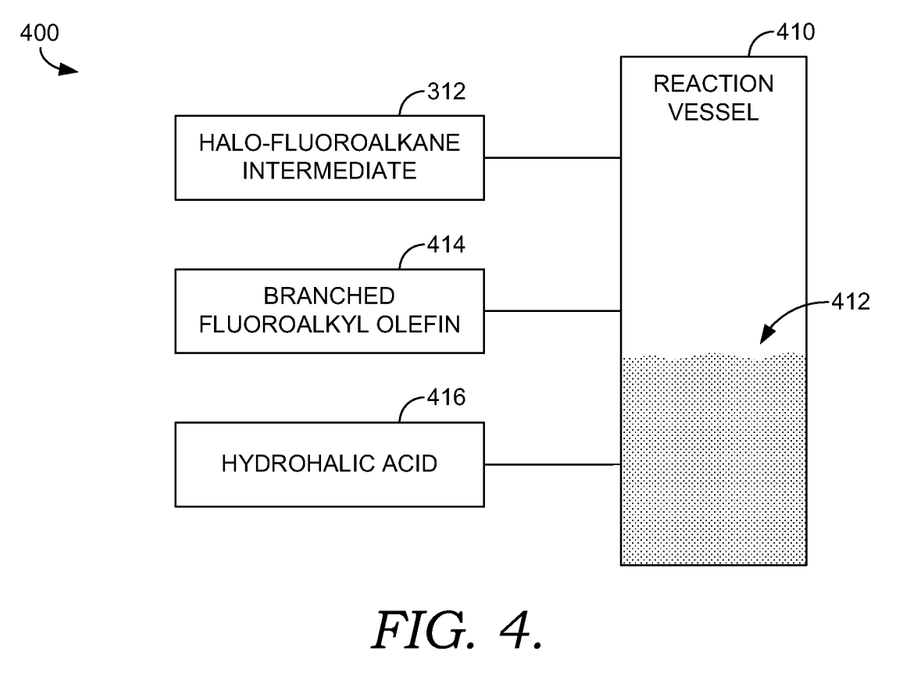
FIG. 4 depicts a schematic diagram of a system for the production of a branched fluoroalkyl olefin.

Turning now to FIG. 4, a system 400 is depicted that includes a halo-fluoroalkane intermediate reservoir 312, which may be coupled to a reaction vessel 410. The system 400 may be configured with the reservoir 312 to produce a branched fluoroalkyl olefin within the branched fluoroalkyl olefin reservoir 414 and/or within at least portion of the reaction vessel 410. In various aspects, as discussed below, the system 400 may be configured with the reaction reservoir 312 to produce a hydrohalic acid, within the hydrohalic acid reservoir 416 and/or within at least a portion of the reaction vessel 410.

In various aspects, the reaction vessel 410 may be configured as a commercially operable reaction vessel. Such reaction vessels may include those reaction vessels configured to react compounds in the liquid phase and/or in the gas phase at predetermined pressures and/or temperatures. In one or more aspects, the reaction vessel 410 may include conduits for receiving halo-fluoroalkane from the reservoir 312. In the same or alternative aspects, conduits for providing product to the reservoirs 414 and/or 416 may be included.

The halo-fluoroalkane intermediate may include any or all of the properties for the halo-fluoroalkane intermediates discussed above with reference to the system 300. For example, the halo-fluoroalkane intermediate may include a compound having the formula:

wherein R is selected from the group consisting of —CH₂CHFBr, —CH₂CCl₂Br, —CH₂CHClBr and —CH₂CF₂Br;

wherein R is selected from the group consisting of —CH₂CH₂Cl, —CH₂CCl₃, —CH₂CF₂Cl, —CH₂CHCl₂, and —CH₂CHClF; or, wherein R is selected from the group consisting of —CH₂CCl₂Br, —CH₂CF₂Br, —CH₂CHClBr and —CH₂CHFBr. In one aspect, the halo-fluoroalkane intermediate may comprise 4-bromo-1,1,1,2,4,-pentafluoro-2-(trifluoromethyl)butane.

In various aspects, one or more halo-fluoroalkane intermediates may be added to a reaction vessel, e.g., the reaction vessel 410, under conditions that can produce one or more branched fluoroalkyl olefins. In such aspects, the one or more halo-fluoroalkane intermediates may be converted to one or more branched fluoroalkyl olefins via a dehydrohalogenation reaction.

In certain aspects, the dehydrohalogenation of a halo-fluoroalkane intermediate may be carried out in the gas phase or in the liquid phase. In various aspects, when the dehydrohalogenation is performed in the liquid phase, a base may be present, such as alkali metal bases or organic bases. In one or more aspects, when the dehydrohalogenation is performed in the gas phase, one or more catalysts, such as activated carbon, alumina oxides, or chrome oxides, may be present.

In certain aspects, a gas phase dehydrohalogenation reaction may include exposing the halo-fluoroalkane to a catalyst, e.g., activated carbon, at a predetermined temperature in a reaction vessel, such as the reaction vessel 410. The predetermined temperature may be at least about 100° C., 125° C., 150° C., or 175° C., and/or not more than about 300° C., 275° C., 250° C., or 225° C. In one aspect, the predetermined temperature may be about 200° C. In an alternative aspect, the predetermined temperature may be about 185° C. In one or more aspects, the contact time between the catalyst and the halo-fluoroalkane intermediate may be at least about 1 second, 2 seconds, 5 second, 10 seconds, 15 seconds, or 20 seconds, and/or not more than about 120 seconds, 100 seconds, 75 seconds, or 60 seconds. In such aspects, the contact time between the catalyst and the halo-fluoroalkane intermediate may be determined based on the flow rate of the gaseous halo-fluoroalkane at 25° C. and/or the flow rate of the gaseous halo-fluoroalkane taking the temperature of the reaction vessel into account.

An exemplary process for the dehydrohalogenation of a halo-fluoroalkane intermediate may include configuring the reaction vessel 410 as a 12 inch by 5 inch Hastelloy® reactor tube. The reactor tube may include at least about 1 mL, 2.5 mL, 5 mL, 6 mL, or 7.5 mL of catalyst, such as coconut shell carbon that may be crushed and sieved to give a particle size distribution of about 12-20 mesh. Further, this exemplary process may include heating the reactor tube to the predetermined temperature while being purged, e.g., with nitrogen. The halo-fluoroalkane intermediate may be added to the reaction tube with a syringe pump at a rate sufficient to provide the desired contact time and/or to produce the desired branched fluoroalkyl olefin.

In certain aspects, the gas phase dehydrohalogenation reaction may produce a hydrohalic acid in addition to producing the branched fluoroalkyl olefin. For example, in such aspects, the dehydrobromination of a halo-fluoroalkane intermediate may produce hydrogen bromide. In one or more embodiments, the system 400 may be configured for the commercial production of hydrogen bromide, e.g., via the dehydrohalogenation of a halo-fluoroalkane intermediate disclosed herein.

An exemplary process for the liquid phase dehydrohalogenation of a halo-fluoroalkane intermediate may include configuring the reaction vessel 410 as a reaction tube. The reaction tube may include a mixture, e.g., a mixture 412 in the reaction vessel 410, of a base, such as an alkali metal base, and a halo-fluoroalkane. The base may be present in an amount sufficient to dehydrohalogenate at least a portion of the halo-fluoroalkane intermediate to produce a branched fluoroalkyl olefin. The liquid phase dehydrogenation may be carried out at between about 0 and about 200° C., preferably between about 35 and about 100° C., with an aqueous and/or alcoholic base. A phase transfer catalyst may also be used to increase rates and yields.

In one or more aspects, the branched fluoroalkyl olefin may include a branched fluorobutene. For example, in such aspects, the branched fluoroalkyl olefin may include 1,3,4,4,4-pentafluoro-3-trifluoromethyl)but-1-ene (HFO-1438ezy). In such aspects, the branched fluoroalkyl olefin may be a mixture of isomers. For example, the branched fluoroalkyl olefin may be present as a mixture of a cis isomer and a trans isomer. In certain aspects, a branched fluoroalkyl olefin, e.g., HFO-1438ezy produced via the processes disclosed herein, may include at least about 1 mole %, 2 mole %, 5 mole %, 10 mole %, or 15 mole % of the cis isomer, and/or not more than about 50 mole %, 40 mole %, 30 mole %, 25 mole %, or 20 mole % of the cis isomer. In the same or alternative aspects, a branched fluoroalkyl olefin, e.g., HFO-1438ezy produced via the processes disclosed herein, may include at least about 40 mole %, 50 mole %, 60 mole %, or 70 mole % of the trans isomer, and/or not more than about 99 mole %, 95 mole %, 90 mole %, 80 mole %, or 75 mole % of the trans isomer. In one or more aspects, a branched fluoroalkyl olefin, e.g., HFO-1438ezy produced via the processes disclosed herein, may exhibit a ratio of the cis isomer to the trans isomer of at least about 1%, 2%, 5%, or 10%, and or not more than about 40%, 30%, 25%, 20%, or 15%.

Below are presented three reaction schemes for the production of HFO-1438ezy that were evaluated.

Reaction Scheme 1: The Dibromide Reaction Scheme

Reaction Scheme 1 involves the addition of 1,2-dibromo-1,1,2,3,3,3-hexafluoropropane to an olefin such as vinyl fluoride. The reaction was run for 24 hours at 100° C. The catalyst used for this reaction was dibenzoyl peroxide. The product, 1,4-dibromo-1,1,2,4-tetrafluoro-2-(trifluoromethyl)butane, was obtained at 54 to 82% yield.

1,4-dibromo-1,1,2,4-tetrafluoro-2-(trifluoromethyl)butane can then be treated with base to form 4-bromo-1,3,4,4-tetrafluoro-3-(trifluoromethy)but-1-ene. 4-bromo-1,3,4,4-tetrafluoro-3-(trifluoromethy)but-1-ene can then be treated with a fluorinating agent to form 1438ezy. The relatively low yield levels of the first step would result in high consumption of 1,2-dibromo-1,1,2,3,3,3-hexafluoropropane as a reactant, and would be expected to necessitate an extra purification step.

Reaction Scheme 2: The Dichloride Reaction Scheme

Reaction Scheme 2 involves the addition of 2,2-dichloro-1,1,1,3,3,3-hexafluoropropane (216aa) to an olefin such as vinyl fluoride. The reaction was run for 24 hours at 110° C. The catalyst used for this reaction was iron. The product, 2,4-dichloro-1,1,1,4-tetrafluoro-2-(trifluoromethyl)butane, was obtained at 94% yield. 2,4-dichloro-1,1,1,4-tetrafluoro-2-(trifluoromethyl)butane was then treated with base such as aqueous KOH solution and a PTC (phase transfer catalyst) such as tetrabutyl ammonium hydrogen sulfate to give 3-chloro-1,4,4,4-tetrafluoro-3-(trifluoromethyl)but-1-ene in a multiple product mixture.

3-chloro-1,4,4,4-tetrafluoro-3-(trifluoromethyl)but-1-ene can be isolated from the product mixture and treated with a fluorinating agent to give 1438ezy. This third step of product isolation is an extra step in the reaction scheme necessitated by the multiple product mixture that results from the second step. The generation of by-products in the second step may pose challenges in recycling or disposal.

Reaction Scheme 3: The Monobromide Reaction Scheme

BP = 15-16 C

Sequence 3(a): Synthesis of 2-bromo heptafluoropropane.

Quantities of 2-bromo heptafluoropropane can be synthesized by the high-temperature bromination of 2H-heptafluoropropane with elemental bromine (lower path). Alternatively, 2-bromo heptafluoropropane may be synthesized by the nucleophilic fluorination of 1,2-dibromo hexafluoropropane (upper path).

Reaction Sequence 3(b): Synthesis of 1438ezy Starting from 2-bromo heptafluoropropane Reaction Sequence 3(b) can be carried out by the addition of 2-bromo heptafluoropropane to an olefin such as vinyl fluoride. The reaction can be carried out at a temperature of from about 110 to about 170° C. using iron as a catalyst and tributyl phosphate or triphenyl phosphine as a ligand. The resulting product 4-bromo-1,1,1,2,4-pentafluoro-2-(trifluoromethy)butane can be expected to be obtained at a yield of >95%. 4-bromo-1,1,1,2,4-pentafluoro-2-(trifluoromethy) butane can then be dehydro brominated to give 1438ezy.

In view of the relatively low yields of the dibromide scheme and the multiple product mixture of the dichloride scheme, Applicants decided that the monobromide scheme was the best candidate for further development.

The present disclosure also provides combustion prevention compositions that may include one or more branched fluoroalkyl olefins described herein. For example, in one or more aspects, a combustion prevention composition may include HFO-1438ezy. The combustion prevention compositions disclosed herein may prevent as well as extinguish combustion through inerting and/or dilution, as well as chemical, physical and/or thermal extinguishment and/or prevention methods. Thermal extinguishing may include "cooling" a combustion.

In certain aspects, the combustion prevention composition may comprise, consist essentially of, and/or consist of one or more branched fluoroalkyl olefins produced via the processes disclosed herein, e.g., HFO-1438ezy.

In one or more aspects, the combustion prevention composition may comprise, consist essentially of, and/or consist of one or more branched fluoroalkyl olefins described above, such as HFO-1438ezy, and a suppressing additive and/or other fire extinguishing agents. The suppressing additive employed may include gases, water, and/or mixtures thereof. Exemplary gases may include nitrogen, argon, helium, carbon dioxide, and/or mixtures thereof. In an exemplary aspect, these gases may deprive fires of necessary fuels, such as oxygen. In the same or other aspects, these gases may resist decomposition when exposed to combustion. In some cases, these gases are referred to as inert gases and/or propellants. An exemplary inert gas may comprise, consist essentially of, and/or consist of nitrogen. In various aspects a propellant, such as nitrogen and/or a hydrofluorocarbon, may be utilized to force the combustion compositions disclosed herein through a nozzle of a combustion composition distribution apparatus.

In certain aspects, the branched fluoroalkyl olefins disclosed herein may be used alone, as admixtures with each other, and/or as blends with other fire extinguishing agents.

The combustion prevention compositions disclosed herein are suitable for use in both total flooding and portable fire suppression applications. Suitable extinguishing agents for blends with the branched fluoroalkyl olefins may include $CF_3CHFCF_3$, $CF_3CF_2CF_2H$, $CF_3CH_2CF_3$, $CF_3CHFCF_2H$, $CF_3CF_2H$, and/or $CF_3H$.

In one or more aspects, the halo-fluoroalkane intermediates and the branched fluoroalkyl olefins can be purified. Purification can be done by any conventional means including distillation, absorption, extraction, chromatography and recrystallization. The term "purified form" as used herein shall be understood to mean at least 99 wt % pure.

In one or more aspects, the combustion prevention compositions disclosed herein may be used in total flooding combustion prevention system in which the composition is introduced to an enclosed region (e.g. a room or other enclosure) surrounding a fire in a concentration sufficient to extinguish the fire. In accordance with the present disclosure, a total flooding system apparatus, equipment, or even rooms of an enclosure may be provided with a source of a composition and appropriate piping valves and controls so as to automatically and/or manually introduce an appropriate concentration in the event that a combustion should occur. Thus, the combustion prevention compositions disclosed herein may be pressurized with nitrogen or other inert gas up to about 600 psig at ambient conditions. Alternatively, the compositions may be applied to combustion through the use of conventional portable fire extinguishing equipment.

A non-limiting list of the applications for the use of the combustion prevention compositions disclosed herein includes the extinguishing of liquid and gaseous fueled fires, the protection of electrical equipment, ordinary combustibles such as wood, paper, and/or textiles, hazardous solids, and the protection of computer facilities, data processing equipment, and control rooms. The combustion prevention compositions disclosed herein may also be introduced to a fire for suppression purposes as a liquid or gas or a combination of both.

In various aspects, the branched fluoroalkyl olefins disclosed herein, such as HFO-1438ezy, may be utilized in a foam expansion agent composition. In such aspects, the foam expansion agent composition may be used in the preparation of polyurethane, polyolefin, and/or polyisocyanurate polymer foams. In addition, in such aspects, the foam expansion agent composition may exhibit volatility that may expand a polymer matrix to form a cellular structure, such as a foam cellular structure found in various insulating materials. In such aspects, one or more branched fluoroalkyl olefins may be present in a foam expansion agent composition. In various aspects, in addition to one or more branched fluoroalkyl olefins, the foam expansion agent composition may include water. In one or more aspects, the foam expansion agent composition may comprise, consist essentially of, and/or consist of one or more branched fluoroalkyl olefins disclosed herein, such as HFO-1438ezy. The foam expansion agent compositions disclosed herein may be utilized in the preparation of polymer foams, e.g., polyurethane and/or polyisocyanurate polymer foams, in any manner known to one skilled in the art.

In various aspects, the branched fluoroalkyl olefins disclosed herein may be utilized in a working fluid for power cycles, such as organic Rankine cycles (ORCs). In one or more aspects, the working fluid may comprise, consist essentially of, and/or consist of one or more branched fluoroalkyl olefins disclosed herein, such as HFO-1438ezy.

In one or more aspects, the working fluids that comprise one or more branched fluoroalkyl olefins disclosed herein may be used in a method for converting heat from a heat source to mechanical energy. In such aspects, heat available at relatively low temperatures compared to steam (inorganic) power cycles can be used to generate mechanical power through organic Rankine cycles, e.g., by using the working fluids disclosed herein. In such aspects, a working fluid comprising one or more branched fluoroalkyl olefins disclosed herein may be compressed prior to being heated. Compression may be provided by a pump, which may pump the working fluid to a heat transfer unit (e.g., a heat exchanger or an evaporator) where heat from the heat source is used to heat the working fluid. The heated working fluid may then expand, lowering its pressure. Mechanical energy may be generated during the working fluid expansion using an expander. Examples of expanders include turbo or dynamic expanders, such as turbines, and positive displacement expanders, such as screw expanders, scroll expanders, and piston expanders. Examples of expanders also include rotary vane expanders.

In various aspects, the generated mechanical power may be used directly (e.g. to drive a compressor) or be converted to electrical power through the use of electrical power generators. In a power cycle where the working fluid is re-used, the expanded working fluid may be cooled. Cooling may be accomplished in a working fluid cooling unit (e.g. a heat exchanger or a condenser). The cooled working fluid may then be used for repeated cycles (i.e., compression, heating, expansion, etc.). The same pump used for compression may be used for transferring the working fluid from the cooling stage.

In certain aspects, one or more branched fluoroalkyl olefins disclosed herein may be utilized in a refrigerant composition for use in a chiller, such as a flooded evaporator chiller and/or a direct expansion chiller. In general, a chiller may produce cooling by using an evaporator to evaporate a refrigerant, e.g. the refrigerant compositions disclosed herein, in order to cool a heat transfer medium located in or adjacent to the evaporator, where the cooled heat transfer medium is then transported to a space or body that is to be cooled. In one or more aspects, the refrigerant composition may comprise, consist essentially of, and/or consist of one or more branched fluoroalkyl olefins disclosed herein, such as HFO-1438ezy.

In certain aspects, the refrigerant compositions disclosed herein may comprise or be utilized in conjunction with a lubricant. In such aspects, the lubricant may include one or more of polyalkylene glycols, polyol esters, polyvinylethers, mineral oils, alkylbenzenes, synthetic paraffins, synthetic naphthenes, and poly(alpha)olefins.

In certain aspects, the branched fluoroalkyl olefins disclosed herein may be utilized in a dielectric fluid composition. In such aspects, the dielectric fluid composition may comprise, consist essentially of, and/or consist of one or more branched fluoroalkyl olefins disclosed herein, such as HFO-1438ezy. In such aspects, the dielectric fluid composition may be utilized to insulate one or more electrical components, such as transformers, capacitors, or electrical wires. In one or more aspects, the dielectric fluid compositions disclosed herein may also transfer heat from one or more electrical components to thereby provide a cooling mechanism.

EXAMPLES

The concepts described herein will be further described in the following examples, which do not limit the scope of the claims.

Example 1

Thermal Bromination of Hexafluoropropylene

This example demonstrates the thermal bromination of hexafluoropropylene (HFP), a fluorine-containing carbon compound disclosed herein.

160 grams of bromine was added into a 400 ml Hastelloy® shaker tube. The tube was then chilled in a dry ice/acetone bath for about 15 minutes and evacuated. The tube was then heated to 100° C. while shaking, and 150 grams of HFP was added at a rate of 1 ml per minute. After adding all the HFP, the tube was maintained at 100° C. for an additional 9 hours. The tube was then chilled in wet ice and the product mixture (309.53 grams) was collected. The mixture was washed twice with 50 ml of 10% aqueous sodium sulfite. The organic layer was dried with 3 A molecular sieves and analyzed by gas chromatography-mass spectrometry (gc/ms). Analysis show 99.41% yield of the desired product.

Example 2

(Prophetic): UV Bromination of Hexafluoropropylene

This example can illustrate suitable conditions for the UV bromination of HFP, a fluorine-containing carbon compound disclosed herein.

200 grams of bromine can be added into a 500 ml 3 neck round bottom flask, which can be equipped with a dry ice condenser. A sunlamp can be used to irradiate UV light onto the outside surface of the flask. HFP gas can be added subsurface into the bromine liquid. The rate of HFP addition can be controlled by the amount of reflux from the dry ice condenser. HFP gas can be fed into the flask until the solution becomes clear or until the appropriate amount has been added. The resulting material can be washed with 10% sodium sulfite (aqueous) to remove any remaining bromine. The organic phase can be dried with calcium sulfate and analyzed by gc/ms. Analysis may show 99% yield of the desired product.

Example 3

Formation of 2-bromoheptafluoropropane (217ba-b)

This example demonstrates the fluorination of 1,2-dibromohexafluoropropane to produce 2-bromoheptafluoropropane, a halo-fluoroalkane reactant disclosed herein.

3 kgs of spray dried potassium fluoride and 10 kgs of sulfolane were added into a 5 gallon stirred autoclave. The autoclave was sealed and 10 kgs of 1,2-dibromohexafluoropropane was added through a dip tube. The autoclave was then evacuated under slight vacuum followed by a $N_2$ purge (2 times each). The autoclave was heated to 125° C. while vigorously stirring for 27 hours. After 27 hours, the autoclave was allowed to cool to 90° C. The agitation was decreased and the product mixture was allowed to vapor transfer into 2 evacuated metal cylinders chilled in a dry ice bath. The cylinders were weighed to give a total net weight of 7.71 kgs of crude product. The crude product was analyzed by gc/ms.

Cylinder #1 had a net wt. of 5.615 kgs, with the $CF_3CFBrCF_3$ product having a 93.41% yield as determined by gc/ms. Cylinder #2 had a net wt. of 2.095 kgs, with the $CF_3CFBrCF_3$ product having a 95.05% yield, as determined by gc/ms.

Example 4

Formation of 2-bromoheptafluoropropane (217ba-B)

This example demonstrates the formation 2-bromoheptafluoropropane (217ba-B), a halo-fluoroalkane reactant disclosed herein.

6 mL of coconut shell carbon (crushed and sieved to give a particle size distribution of 12-20 mesh) was added into a 12" by 0.5" Hastelloy® tube reactor. The reactor was then heated to the desired temperature while purging with 2H-heptafluoropropane. Liquid bromine was then fed to the reactor with a syringe pump through a vaporizer at 150° C. The feed rates of 2H-heptafluoropropane and bromine were adjusted to give the desired contact time listed in Table 1 below. Table 2 lists the effect of reactor temperature on the bromination of 2H-heptafluoropropane.

TABLE 1

Effect of Contact Time on 2H-heptafluoropropane Bromination

| | Run # | Mole % | | | | | | Furnace Temp ° C. | CT sec | Ratio Br2/227ea |
|---|---|---|---|---|---|---|---|---|---|---|
| | | others | 218 | HFP | 1225zc | 227ea | 217baB | | | |
| 45 sec | 1 | 0.86% | 0.00% | 0.93% | 0.00% | 17.97% | 80.24% | 450 | 44.5 | 1.4 : 1 |
| | 2 | 1.64% | 0.00% | 0.41% | 0.00% | 21.75% | 76.20% | 450 | 44.5 | 1.4 : 1 |
| | 3 | 1.13% | 0.00% | 1.04% | 0.00% | 21.31% | 76.52% | 451 | 44.5 | 1.4 : 1 |
| | 4 | 1.48% | 0.00% | 0.51% | 0.00% | 21.91% | 76.10% | 450 | 44.5 | 1.4 : 1 |
| | average | 1.28% | 0.00% | 0.72% | 0.00% | 20.73% | 77.27% | | | |
| | | | | | | byproduct/ | product | | | |
| | | | | | | | 2.21% | | | |
| 30 sec | 5 | 0.66% | 0.00% | 0.84% | 0.00% | 31.73% | 66.77% | 450 | 29.9 | 1.2 : 1 |
| | 6 | 0.92% | 0.00% | 0.41% | 0.00% | 33.17% | 65.51% | 450 | 29.9 | 1.2 : 1 |
| | 7 | 0.60% | 0.00% | 0.77% | 0.00% | 31.70% | 66.92% | 450 | 29.9 | 1.2 : 1 |
| | 8 | 0.88% | 0.00% | 0.53% | 0.00% | 32.73% | 65.85% | 450 | 29.9 | 1.2 : 1 |
| | average | 0.77% | 0.00% | 0.64% | 0.00% | 32.33% | 66.26% | | | |
| | | | | | | byproduct/ | product | | | |
| | | | | | | | 1.73% | | | |
| 15 sec | 9 | 0.25% | 0.00% | 0.29% | 0.00% | 50.12% | 49.34% | 450 | 15.2 | 1.2 : 1 |
| | 10 | 0.30% | 0.00% | 0.23% | 0.00% | 53.00% | 46.47% | 450 | 15.2 | 1.2 : 1 |
| | 11 | 0.25% | 0.00% | 0.29% | 0.00% | 50.48% | 48.98% | 450 | 15.2 | 1.2 : 1 |

TABLE 1-continued

Effect of Contact Time on 2H-heptafluoropropane Bromination

| | | Mole % | | | | | Furnace | CT | Ratio |
|---|---|---|---|---|---|---|---|---|---|
| Run # | others | 218 | HFP | 1225zc | 227ea | 217baB | Temp ° C. | sec | Br2/227ea |
| 12 | 0.19% | 0.00% | 0.37% | 0.00% | 45.19% | 54.25% | 450 | 15.2 | 1.2 : 1 |
| average | 0.25% | 0.00% | 0.30% | 0.00% | 49.69% | 49.76% | | | |
| | | | | | byproduct/ product | 0.84% | | | |

218 = HFC 218 (1,1,1,2,2,3,3,3-octafluoropropane)
1225zc = (FC-1225 zc (1,1,3,3,3-pentafluoropropene-1)
227ea = 2H-heptalfuoropropane
217baB = 2-bromoheptafluoropropane (product)
CT = contact time
byproduct = the total cumulative mole percent of the products: others, 218, HFP, and 1225Zc.

TABLE 2

Effect of Temperature on 2H-heptafluoropropane Bromination

| | Run # | others | 218 | HFP | 1225zc | 227ea | 217baB | Furnace Temp ° C. | CT sec | Ratio Br2/227ea |
|---|---|---|---|---|---|---|---|---|---|---|
| 450° C. | 1 | 1.69% | 0.00% | 1.18% | 0.00% | 12.79% | 84.34% | 450 | 46.8 | 1.3 : 1 |
| | 2 | 1.95% | 0.00% | 1.53% | 0.00% | 13.82% | 82.70% | 450 | 46.7 | 1.3 : 1 |
| | 3 | 1.87% | 0.00% | 2.20% | 0.00% | 14.43% | 81.50% | 450 | 46.7 | 1.3 : 1 |
| | 4 | 2.53% | 0.00% | .41% | 0.00% | 14.35% | 82.72% | 451 | 46.9 | 1.3 : 1 |
| | average | 2.01% | 0.00% | 1.33% | 0.00% | 13.85% | 82.81% | | | |
| | | | | | | byproduct/ product | 3.62% | | | |
| 425° C. | 5 | 0.32% | 0.00% | 0.35% | 0.00% | 30.18% | 69.15% | 425 | 46.8 | 1.3 : 1 |
| | 6 | 0.44% | 0.00% | 0.31% | 0.00% | 29.37% | 69.87% | 425 | 46.7 | 1.3 : 1 |
| | 7 | 0.26% | 0.00% | 0.45% | 0.00% | 27.81% | 71.48% | 425 | 46.9 | 1.3 : 1 |
| | 8 | 0.47% | 0.00% | 0.38% | 0.00% | 32.34% | 66.80% | 425 | 46.8 | 1.3 : 1 |
| | average | 0.37% | 0.00% | 0.37% | 0.00% | 29.93% | 69.33% | | | |
| | | | | | | byproduct/ product | 0.91% | | | |
| 400° C. | 9 | 0.08% | 0.00% | 0.05% | 0.00% | 56.49% | 43.38% | 400 | 46.9 | 1.3 : 1 |
| | 10 | 0.07% | 0.00% | 0.08% | 0.00% | 51.33% | 48.52% | 400 | 46.9 | 1.3 : 1 |
| | 11 | 0.10% | 0.00% | 0.03% | 0.00% | 59.18% | 40.68% | 400 | 46.8 | 1.3 : 1 |
| | average | 0.08% | 0.00% | 0.06% | 0.00% | 55.67% | 44.19% | | | |
| | | | | | | byproduct/ product | 0.21% | | | |

218, 1225zc, 227ea, 217baB, byproduct, and CT have the same meaning as for Table 1 above.

Example 5

Formation of 4-bromo-1,1,1,2,4-pentafluoro-2-(trifluoromethyl)butane

This example demonstrates the formation of 4-bromo-1,1,1,2,4-pentafluoro-2-(trifluoromethyl)butane, a halo-fluoroalkane intermediate disclosed herein.

5.6 grams of iron powder, 2.5 grams of iron III bromide, and 13.5 grams of tributyl phosphate were added into a 400 ml shaker tube. The tube was then chilled in a dry ice/acetone bath and 250 grams of 2-bromoheptafluoropropane was added therein. The tube was then flushed with $N_2$ and evacuated (2 times each). The tube was then heated to 120° C. while shaking for 2 hours. After 2 hours, 46 grams of vinyl fluoride was added over 2 hours. After addition of all of the vinyl fluoride, the tube was held at 120° C. while shaking for an additional 24 hrs. After 24 hours, the tube was chilled in wet ice. The crude product was collected and gc/ms showed a 88.7% yield of 4-bromo-1,1,1,2,4-pentafluoro-2-(trifluoromethyl)butane.

Example 6

Formation of 4-bromo-1,1,1,2,4-pentafluoro-2-(trifluoromethyl)butane

This example demonstrates the formation of 4-bromo-1,1,1,2,4-pentafluoro-2-(trifluoromethyl)butane, a halo-fluoroalkane intermediate disclosed herein.

4.2 grams of iron powder, 2 grams of iron III bromide, and 9.8 grams of triphenyl phosphine were added into a 400 ml shaker tube. The tube was chilled in a dry ice/acetone bath and then 250 grams of 2-bromoheptafluoropropane was added. The tube was then flushed with $N_2$ and evacuated (2 times each). The tube was then heated to 170° C. while shaking for 2 hours. After 2 hours, 46 grams of vinyl fluoride was added over 2 hours. After addition of all the vinyl fluoride, the tube was held at 170° C. while shaking for an additional 24 hrs. After 24 hours, the tube was chilled in wet ice. The crude product was collected and gc/ms revealed an 83.9% yield of 4-bromo-1,1,1,2,4-pentafluoro-2-(trifluoromethyl)butane.

Example 7a

Formation of 1,4-dibromo-1,1,2,4-tetrafluoro-2-(trifluoromethyl)butane

This example demonstrates the formation of 1,4-dibromo-1,1,2,4-tetrafluoro-2-(trifluoromethyl)butane, a halo-fluoroalkane intermediate disclosed herein.

Reaction Scheme:

$CF_3-CFBr-CF_2Br+CH_2=CHF \rightarrow CF_3-CF(CF_2Br)-CH_2-CHFBr$ 310 grams of 1,2-dibromo-hexafluoropropane (216ba-b2) and 1 gram of dibenzoyl peroxide were added to a 400 ml shaker tube. The tube was chilled in a dry ice/acetone bath and evacuated. The tube was then heated to 100° C. for 30 minutes. After 30 minutes, 8 grams of vinyl fluoride was added over a 1 hour period. After addition of all the vinyl fluoride, the tube was heated for an additional 24 hours. After 24 hours, the tube was then allowed to cool to room temperature and the resulting product mixture was analyzed by gc/ms. An 82.19% yield of 1,4-dibromo-1,1,2,4-tetrafluoro-2-(trifluoromethyl)butane was observed.

Example 7b

Formation of 1,4-dibromo-1,1,2,4-tetrafluoro-2-(trifluoromethyl)butane

This example demonstrates the formation of 1,4-dibromo-1,1,2,4-tetrafluoro-2-(trifluoromethyl)butane with differing amounts of dibenzoyl peroxide and vinyl fluoride. Particularly, the procedure was performed as described above in Example 7a except that 2 grams of dibenzoyl peroxide and 41 grams of vinyl fluoride were utilized. Gc/ms revealed a 54.75% yield of 1,4-dibromo-1,1,2,4-tetrafluoro-2-(trifluoromethyl)butane.

Example 7c

Formation of 1,4-dibromo-1,1,2,4-tetrafluoro-2-(trifluoromethyl)butane

Reaction Scheme:

$CF_3-CFBr-CF_2Br+CH_2=CH_2 \rightarrow CF_3-CF(CF_2Br)-CH_2-CH_2Br$

This example demonstrates the formation of 1,4-dibromo-1,1,2,4-tetrafluoro-2-(trifluoromethyl)butane with different reactants. Particularly, the procedure was performed as described above in Example 7a except that 150 grams of 1,4-dibromo-1,1,2-trifluoro-2-(trifluoromethyl)butane and 8 grams of ethylene were added instead of 216ba-b2 and the vinyl fluoride, respectively. Gc/ms revealed a 74.64% yield of 1,4-dibromo-1,1,2,4-tetrafluoro-2-(trifluoromethyl)butane.

Example 8

Addition of 2,2-dichloro-1,1,1,3,3,3-hexafluoropropane (216aa) to olefins

This example demonstrates the formation of various halo-fluoroalkane intermediates disclosed herein.

216aa and a catalyst were added to a pressure reactor. Table 3 below lists the amounts of 216aa and the amounts and types of catalysts used. The reactor was chilled in a dry ice/acetone bath. The reactor was flushed with $N_2$ and evacuated (2 times each). The reactor was then heated to 110° C. for 1 hour. Then the olefin, listed below in Table 3, was added over a 1 hour period. After addition of the olefin, the reaction was allowed to continue for an additional 24 hours. The reactor was allowed to cool and the product mixture and the yield were analyzed by gc/ms. Table 3 lists the results, and the desired products are listed below Table 3.

TABLE 3

Product yield for the addition of 216aa to olefins

| Run # | Reactants and Amounts | Catalyst and Amounts | Run Temp. (° C.) | Run Time | Yield of Desired Product |
|---|---|---|---|---|---|
| 1 | 216aa/Vinyl fluoride 221 gr/8 gr 5.8/1 mole ratio | Iron wire/FeCl$_3$/ Tributyl phosphate 1.5 gr/0.6 gr/3.3 gr | 110 | 24 hrs | 94.56% |
| 2 | 216aa/ethylene 221 gr/8 gr 3.5/1 mole ratio | Iron wire/FeCl$_3$/ Tributyl phosphate 1.5 gr/0.6 gr/3.3 gr | 110 | 24 hrs | 87.25% |
| 3 | 216aa/vinyl chloride 221 gr/10 gr 6/1 mole ratio | Iron wire/FeCl$_3$/ Tributyl phosphate 1.5 gr/0.6 gr/3.3 gr | 110 | 24 hrs | 87.83% |

The desired product for Run 1 has the formula:

$$\begin{array}{c} CF_3CClCF_3 \\ | \\ CH_2CHClF \end{array}$$

2,4-dichloro-1,1,1,4-tetrafluoro-2-(trifluoromethyl)butane. The desired product for Run 2 has the formula:

$$\begin{array}{c} CF_3CClCF_3 \\ | \\ CH_2CH_2Cl \end{array}$$

2,4-dichloro-1,1,1-trifluoro-2-(trifluoromethyl)butane. The desired product for Run 3 has the formula:

$$\begin{array}{c} CF_3CClCF_3 \\ | \\ CH_2CHCl_2 \end{array}$$

2,4,4-trichloro-1,1,1-trifluoro-2-(trifluoromethyl)butane.

Example 9

Formation of E-1,3,4,4,4-pentafluoro-3-(trifluoromethyl)but-1-ene (HFO-1438ezy)

This example demonstrates the formation of HFO-1438ezy, a branched fluoroalkyl olefin disclosed herein.

Figure 5:
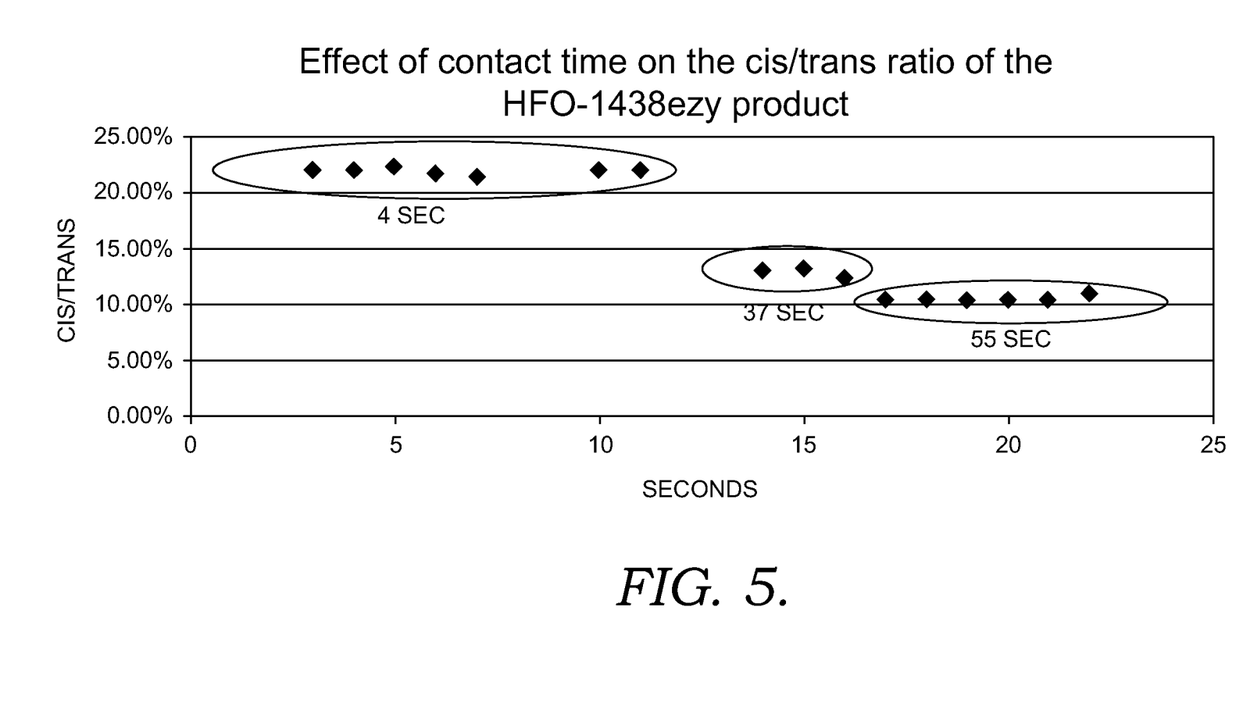
FIG. 5 depicts a graph illustrating the effect of the contact time of 4-bromo-1,1,1,2,4-pentafluoro-2-(trifluoromethyl) butane to carbon on the cis/trans ratio of the 1,3,4,4,4-pentafluoro-3-(trifluoromethyl)but-1-ene product.

6 cc of coconut shell carbon (crushed and sieved to give a particle size distribution of 12-20 mesh) was added into a 12 inch by 0.5 inch Hastelloy® tube reactor. The reactor was then heated to the desired temperature while purging with $N_2$ (the desired temperatures are provided below in Tables 4 and 5). Then, 4-bromo-1,1,1,2,4-pentafluoro-2-(trifluoromethyl)butane was fed into the reactor with a syringe pump. The feed rates of 4-bromo-1,1,1,2,4-pentafluoro-2-(trifluoromethyl)butane and $N_2$ were adjusted to give the desired contact times listed in Tables 4 and 5 below. In addition, as discussed below, FIG. 5 provides a graphical illustration of the effect of contact time on the ratio of the cis isomer to the trans isomer of the HFO-1438ezy product.

TABLE 4

Effect of Contact Time on the Formation of HFO-1438ezy

| | | | Mole % | | | | | |
|---|---|---|---|---|---|---|---|---|
| run | Others | HFP | (E)-HFO-1438ezy | (Z)-HFO-1438ezy | F7VFBr | Z/E | Furnace Temp ° C. | C T (sec) |
| 1 | 3.11% | 0.00% | 85.39% | 10.38% | 1.12% | 12.16% | 200 | 15.6 |
| 2 | 2.34% | 0.00% | 81.96% | 13.82% | 1.89% | 16.86% | 200 | 15.6 |
| 3 | 4.22% | 0.00% | 81.58% | 14.20% | 0.00% | 17.40% | 200 | 15.6 |
| 4 | 4.26% | 0.00% | 81.03% | 14.72% | 0.00% | 18.16% | 200 | 15.5 |
| 5 | 7.28% | 0.00% | 79.44% | 12.35% | 0.93% | 15.54% | 220 | 15.6 |
| 6 | 9.17% | 0.00% | 77.87% | 12.12% | 0.84% | 15.56% | 220 | 15.6 |
| 7 | 4.99% | 0.00% | 77.64% | 17.36% | 0.00% | 22.37% | 200 | 6.2 |
| 8 | 4.40% | 0.00% | 78.03% | 17.57% | 0.00% | 22.52% | 200 | 6.2 |
| 9 | 1.39% | 0.00% | 79.00% | 16.38% | 3.23% | 20.73% | 200 | 6.2 |
| 10 | 1.13% | 0.00% | 78.02% | 17.55% | 3.31% | 22.50% | 199 | 4.8 |
| 11 | 0.97% | 0.00% | 74.64% | 16.91% | 7.47% | 22.66% | 200 | 4.8 |
| 12 | 8.80% | 0.17% | 74.02% | 16.85% | 0.00% | 22.76% | 200 | 4.8 |
| 13 | 1.17% | 0.18% | 72.28% | 16.30% | 10.07% | 22.55% | 200 | 4.8 |
| 14 | 3.17% | 0.00% | 78.57% | 17.61% | 0.65% | 22.41% | 220 | 4.8 |
| 15 | 3.00% | 0.00% | 78.58% | 17.71% | 0.72% | 22.54% | 220 | 4.8 |
| 16 | 3.63% | 0.00% | 78.65% | 17.72% | 0.00% | 22.53% | 220 | 4.8 |
| 17 | 1.23% | 0.00% | 79.35% | 19.42% | 0.00% | 24.47% | 197 | 3 |
| 18 | 0.82% | 0.25% | 67.30% | 15.19% | 16.43% | 22.57% | 200 | 3 |
| 19 | 0.46% | 0.40% | 68.73% | 15.62% | 14.78% | 22.73% | 200 | 3 |

TABLE 5

Effect of Contact Time on the Formation of HFO-1438ezy

| | | | Mole % | | | | | | |
|---|---|---|---|---|---|---|---|---|---|
| Run # | others | 217ba-b | (E)-HFO-1438ezy | (Z)-HFO-1438ezy | F7VF Br | Z/E | Furnace Temp ° C. | $N_2$ (sccm) | CT sec |
| 1 | | | | | | | | | |
| 2 | | | | | | | | | |
| 4 | 1.27% | 0.00% | 79.44% | 17.46% | 1.83% | 21.97% | 200 | 88.24 | 3.8 |
| 5 | 0.59% | 0.00% | 79.12% | 17.36% | 2.93% | 21.94% | 200 | 88.25 | 3.8 |
| 6 | 0.67% | 0.00% | 79.50% | 17.63% | 2.21% | 22.17% | 200 | 88.26 | 3.8 |
| 7 | 0.45% | 0.00% | 56.71% | 12.23% | 30.61% | 21.57% | 185 | 88.25 | 3.8 |
| 8 | 0.00% | 0.00% | 60.59% | 12.93% | 26.48% | 21.33% | 185 | 88.25 | 3.8 |
| 9 | | | | | | | | | |
| 10 | | | | | | | | | |
| 11 | 0.84% | 0.00% | 79.10% | 17.33% | 2.74% | 21.91% | 200 | 88.24 | 3.8 |
| 12 | 0.58% | 0.00% | 79.08% | 17.37% | 2.96% | 21.97% | 201 | 88.26 | 3.8 |
| 13 | | | | | | | | | |
| 14 | | | | | | | | | |
| 15 | 2.91% | 0.08% | 80.88% | 10.44% | 5.59% | 12.91% | 185 | 7.57 | 36.5 |
| 16 | 2.15% | 0.08% | 80.88% | 10.64% | 6.15% | 13.16% | 185 | 7.48 | 36.8 |
| 17 | 2.15% | 0.09% | 81.87% | 10.08% | 5.70% | 12.31% | 185 | 7.57 | 39.3 |
| 18 | 2.58% | 0.08% | 82.41% | 8.59% | 6.22% | 10.43% | 186 | 4.93 | 55.2 |
| 19 | 2.87% | 0.08% | 82.28% | 8.53% | 6.12% | 10.36% | 185 | 5.00 | 54.6 |
| 20 | 3.05% | 0.08% | 82.24% | 8.50% | 6.04% | 10.34% | 185 | 4.94 | 55.2 |
| 21 | 3.19% | 0.08% | 82.13% | 8.52% | 6.08% | 10.37% | 185 | 4.91 | 55.4 |
| 22 | 3.23% | 0.08% | 82.08% | 8.46% | 6.07% | 10.31% | 185 | 4.97 | 54.9 |
| 23 | 5.30% | 0.00% | 80.82% | 8.80% | 5.07% | 10.89% | 185 | 4.97 | 54.9 |

F7VFBr, CT, (E)-HFO-1438ezy, (Z)-HFO-1438ezy, and Z/E have the same meaning as in Table 4 above $N_2$ sccm = $N_2$ amount in standard cubic centimeters per minute FIG. 5 graphically illustrates the relationship between the contact time and the cis isomer/trans isomer ratio of the HFO-1438ezy product. As can be seen in FIG. 5, generally, an increased contact time decreases the amount of the cis isomer formed. Contact times of from about 30 to about 60 seconds appear to effectively suppress the yield of the less desirable cis isomer.

Example 10

Addition of Olefins to 2-bromo-1,1,1,2,3,3,3-heptafluoropropane

This example can illustrate the addition of various olefins to 2-bromo-1,1,1,2,3,3,3-heptafluoropropane to produce various halo-fluoroalkane intermediates disclosed herein.

4.2 grams of iron powder, 2 grams of iron III bromide, and 9.8 grams of triphenyl phosphine can be added into a 400 ml shaker tube. The tube can then be chilled in a dry ice/acetone bath, and then 1 mole of 2-bromo-1,1,1,2,3,3,3-heptafluoropropane can be added. The tube can then be flushed with $N_2$ and evacuated (2 times each). The tube can then be heated to 170° C. while shaking for 2 hours. After 2 hours, 1 mole of olefinic reactant can be added over 2 hours. After addition of all the olefinic reactant, the tube can be held at 170° C. while shaking for an additional 24 hrs. After 24 hours, the tube can be chilled in wet ice. The crude product can be collected and gc/ms can be used to reveal a yield of at least about 75% of the desired product. Table 6 below lists the olefinic reactants and the desired products.

TABLE 6

Olefinic Reactants and Halo-Fluoroalkane Intermediates for
the Addition of 2-1,1,1,2,3,3,3-bromo-heptafluoropropane
to Various Olefins, as well as potential
Dehydrohalogenation Product of the Addition Product

| Olefinic Reactant | Halo-Fluoroalkane Intermediate | Dehydrohalogenation Product |
|---|---|---|
| $CH_2$=CHF (Actual) | $CF_3CFCF_3$ \| $CH_2CHFBr$ | E—$(CF_3)_2CF$—CH=CFH |
| $CH_2$=CHCl (Prophetic) | $CF_3CFCF_3$ \| $CH_2CHClBr$ | E—$(CF_3)_2CF$—CH=CClH |
| $CH_2$=$CF_2$ (Prophetic) | $CF_3CFCF_3$ \| $CH_2CF_2Br$ | $(CF_3)_2CF$—CH=$CF_2$ |
| $CH_2$=$CCl_2$ (Prophetic) | $CF_3CFCF_3$ \| $CH_2CCl_2Br$ | $(CF_3)_2CF$—CH=$CCl_2$ |
| $CH_2$=$CH_2$ (Prophetic) | $CF_3CFCF_3$ \| $CH_2CH_2Br$ | $(CF_3)_2CF$—CH=$CH_2$ |

In Table 6, the parenthetical entry beneath the entry for "Olefinic Reactants" indicates whether the indicated reaction was actually carried out ("Actual"), or whether the table entries constitute a prophetic example ("Prophetic"). Only the reaction associated with $CH_2$=CHF as the olefinic reactant (the first table entry) was actually carried out, the remainder being prophetic examples.

Example 11

Addition of Olefins to 216aa
(2,2-dichloro-1,1,1,3,3,3-hexafluoropropane)

This example can illustrate the addition of various olefins to 216aa to produce various halo-fluoroalkane intermediates disclosed herein.

4.2 grams of iron powder, 2 grams of iron III bromide, and 9.8 grams of triphenyl phosphine can be added into a 400 ml shaker tube. The tube can then be chilled in a dry ice/acetone bath, and then 1 mole of 216aa can be added. The tube can then be flushed with $N_2$ and evacuated (2 times each). The tube can then heated to 170° C. while shaking for 2 hours. After 2 hours, 1 mole of olefinic reactant can be added over 2 hours. After addition of all the olefinic reactant, the tube can be held at 170° C. while shaking for an additional 24 hrs. After 24 hours, the tube can be chilled in wet ice. The crude product can be collected and gc/ms can be used to reveal a yield of at least about 75% of the desired product. Table 7 below lists the olefinic reactants and the desired products.

TABLE 7

Olefinic Reactants and Halo-Fluoroalkane
Intermediates for the Olefinic Addition to 216aa, as well as
potential Dehydrohalogenation Product of the Addition Product

| Olefinic Reactant | Halo-Fluoroalkane Intermediate | Potential Dehydrohalogenation Product |
|---|---|---|
| $CH_2$=$CF_2$ | $CF_3CClCF_3$ \| $CH_2CF_2Cl$ | $(CF_3)_2CCl$—CH=$CH_2$ |
| $CH_2$=$CCl_2$ | $CF_3CClCF_3$ \| $CH_2CCl_3$ | E—$(CF_3)_2CCl$—CH=$CCl_2$ |

Example 12

Addition of Olefins to
1,2-dibromo-1,1,2,3,3,3-hexafluoropropane

This example can illustrate the addition of various olefins to 1,2-dibromo-1,1,2,3,3,3-hexafluoropropane to produce various halo-fluoroalkane intermediates disclosed herein.

4.2 grams of iron powder, 2 grams of iron III bromide, and 9.8 grams of triphenyl phosphine can be added into a 400 ml shaker tube. The tube can then be chilled in a dry ice/acetone bath, and then 1 mole of 1,2-dibromo-1,1,2,3,3,3-hexafluoropropane can be added. The tube can then be flushed with $N_2$ and evacuated (2 times each). The tube can then be heated to 170° C. while shaking for 2 hours. After 2 hours, 1 mole of olefinic reactant can be added over 2 hours. After addition of all the olefinic reactant, the tube can be held at 170° C. while shaking for an additional 24 hrs. After 24 hours, the tube can be chilled in wet ice. The crude product can be collected and gc/ms can be used to reveal a yield of at least about 75% of the desired product. Table 8 below lists the olefinic reactants and the desired products.

TABLE 8

Olefinic Reactants and Halo-Fluoroalkane Intermediates for
the Olefinic Addition to
1,2-dibromo-1,1,2,3,3,3-hexafluoropropane, as well as
potential Dehydrohalogenation Product of the Addition Product

| Olefinic Reactant | Halo-Fluoroalkane Intermediate | Dehydrohalogenation Product |
|---|---|---|
| $CH_2$=CHF (Actual) | $CF_3CFCF_2Br$ \| $CH_2CHFBr$ | $(CF_2Br)(CF_3)CF$—CH=$CH_2$ |
| $CH_2$=CHCl (Prophetic) | $CF_3CFCF_2Br$ \| $CH_2CHClBr$ | E—$(CF_2Br)(CF_3)CF$—CH=CHCl |
| $CH_2$=$CF_2$ (Prophetic) | $CF_3CFCF_2Br$ \| $CH_2CF_2Br$ | E—$(CF_2Br)(CF_3)CF$—CH=$CF_2$ |
| $CH_2$=$CCl_2$ (Prophetic) | $CF_3CFCF_2Br$ \| $CH_2CCl_2Br$ | E—$(CF_2Br)(CF_3)CF$—CH=$CCl_2$ |

TABLE 8-continued

Olefinic Reactants and Halo-Fluoroalkane Intermediates for the Olefinic Addition to 1,2-dibromo-1,1,2,3,3,3-hexafluoropropane, as well as potential Dehydrohalogenation Product of the Addition Product

| Olefinic Reactant | Halo-Fluoroalkane Intermediate | Dehydrohalogenation Product |
|---|---|---|
| $CH_2$=$CH_2$ (Actual) | $CF_3CFCF_2Br$<br>\|<br>$CH_2CH_2Br$ | E—$(CF_2Br)(CF_3)CF$—CH=CHF |

In Table 8, the parenthetical entry beneath the entry for "Olefinic Reactants" indicates whether the indicated reaction was actually carried out ("Actual"), or whether the table entries constitute a prophetic example ("Prophetic"). Only the reactions associated with $CH_2$=CHF and $CH_2$=$CH_2$ as the olefinic reactant (the first and last entries in Table 8) were actually carried out, the remainder being prophetic examples.

Example 13

Liquid Phase Formation of E-1,3,4,4,4-pentafluoro-3-(trifluoromethyl)but-1-ene (HFO-1438ezy)

Into a 3-neck round bottom flask, equipped with a mechanical stirrer, Dean-Stark apparatus with a condenser and an addition funnel, can be added 50 grams of 4-bromo-1,1,1,2,4-pentafluoro-2-(trifluoromethyl)butane and 2.5 grams of Aliquat® 336 (PTC). The flask can be heated while stirring to 60° C. 150 ml of 35% aqueous KOH (wt/wt) can be added through the addition funnel. The product, E-1,3,4,4,4-pentafluoro-3-(trifluoromethyl)but-1-ene, can be collected as it is formed into the Dean-Stark apparatus. The product can then be dried and distilled to an expected 99.9% purity.

Example 14

Purification of HFO-1438ezy

Into a 2 liter 3 kneck round bottom flask, equipped with a distillation column (9 inch silver insulated column packed with Z210544 Pro-Pak® distillation packing 0.16 in.2, Monel® from Sigma-Aldrich) and a reflux head with condenser, was added 1492.2 grams of 1,3,4,4,4-pentafluoro-3-(trifluoromethyl)but-1-ene mixture (starting GC purity 87.38% E isomer). The flask was heated slowly to obtain reflux at head of column. Fractions of the distillate were collected from the distillation head and analyzed by GC/MS. Distillate fractions with a boiling point of 30° C. were combined to give 1008.4 grams of 1,3,4,4,4-pentafluoro-3-(trifluoromethyl)but-1-ene (HFO-1438ezy, GC purity of 99.94%).

From the foregoing, it will be seen that this disclosure is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible aspects may be made of the disclosure herein without departing from the scope thereof, it is to be understood that all matter herein set forth or shown in the accompanying drawings is to be interpreted as illustrative and not in a limiting sense.

What is claimed is:

1. A process comprising the step of contacting 2-bromo-heptafluoropropane with vinyl fluoride in the presence of a catalyst, wherein said catalyst is selected from the group consisting of iron, copper and the chloride and bromide salts thereof.

2. The process of claim 1, wherein the catalyst further comprises a ligand, selected from the group consisting of trialkyl phosphate, triphenyl phosphine, and 2,2-Bipyridyl.

3. The process of claim 2, wherein the trialkyl phosphate is tributyl phosphate.

4. The process of claim 1, wherein there is at least from 0.01 moles to 0.1 moles of catalyst per mole of 2-bromo-heptafluoropropane.

5. The process of claim 2, wherein thee is at least from 0.0001 to 0.01 moles of ligand per mole of 2-bromoheptafluoropropane.

6. The process of claim 1, wherein the molar ratio of vinyl fluoride to 2-bromopropane is from 8:1 to 1:8.

7. The process of claim 1, wherein the 2-bromoheptafluoropropane is contacted with vinyl fluoride in the presence of catalyst at a temperature of from 75 C. to 300 C.

8. The process of claim 1, wherein the 2-bromoheptafluoropropane is contacted with vinyl fluoride in the presence of catalyst at a temperature of from 125 C. to 175 C.

* * * * *